(12) United States Patent
Jahangir

(10) Patent No.: US 11,524,137 B2
(45) Date of Patent: Dec. 13, 2022

(54) CANNULA HAVING NITINOL REINFORCED INFLOW REGION

(71) Applicant: Abiomed, Inc., Danvers, MA (US)

(72) Inventor: Emilia Jahangir, Danvers, MA (US)

(73) Assignee: Abiomed, Inc., Danvers, MA (US)

( * ) Notice: Subject to any disclaimer, the term of this patent is extended or adjusted under 35 U.S.C. 154(b) by 555 days.

(21) Appl. No.: 16/598,835

(22) Filed: Oct. 10, 2019

(65) Prior Publication Data

US 2020/0038571 A1 Feb. 6, 2020

Related U.S. Application Data

(62) Division of application No. 15/463,156, filed on Mar. 20, 2017, now Pat. No. 10,478,542.

(51) Int. Cl.
| | |
|---|---|
| *A61M 25/00* | (2006.01) |
| *A61M 60/135* | (2021.01) |
| *A61M 60/148* | (2021.01) |
| *A61M 60/414* | (2021.01) |
| *A61M 60/857* | (2021.01) |
| *A61M 60/216* | (2021.01) |
| *A61M 60/408* | (2021.01) |

(52) U.S. Cl.
CPC .... *A61M 25/0012* (2013.01); *A61M 25/0009* (2013.01); *A61M 25/0015* (2013.01); *A61M 60/135* (2021.01); *A61M 60/148* (2021.01); *A61M 60/216* (2021.01); *A61M 60/408* (2021.01); *A61M 60/414* (2021.01); *A61M 60/857* (2021.01)

(58) Field of Classification Search
CPC ............ A61M 25/0009; A61M 25/112; A61M 25/0013; A61M 25/0015; A61M 1/125; A61M 1/122; A61M 1/1034; A61M 1/1008; A61M 1/101; A61M 1/1012
See application file for complete search history.

(56) References Cited

U.S. PATENT DOCUMENTS

| | | | |
|---|---|---|---|
| 8,377,036 B2 * | 2/2013 | Jonkman | A61M 25/0054 604/536 |
| 8,795,576 B2 * | 8/2014 | Tao | A61M 60/13 264/340 |
| 2011/0004046 A1 | 1/2011 | Campbell et al. | |
| 2015/0141842 A1 | 5/2015 | Spanier et al. | |
| 2018/0055979 A1 | 3/2018 | Corbett et al. | |

* cited by examiner

*Primary Examiner* — Christopher J Besler
(74) *Attorney, Agent, or Firm* — Botos Churchill IP Law LLP

(57) ABSTRACT

An intravascular heart pump assembly can include a rotor with at least one impeller blade, and a cannula. The present application describes various cannulas that can be manufactured from multiple layers of material to improve flexibility, manufacturability, and durability without increasing an outer diameter of the cannula. In one embodiment, the cannula includes an inflow section having a sheet formed of a shape memory material embedded within a polymer and having at least one lateral hole or aperture in the inflow section. The at least one lateral hole is defined by a first hole in the sheet and a second hole in the outer polymer layer of the cannula. The first hole and the second hole overlap so that blood can enter the cannula through the holes.

11 Claims, 9 Drawing Sheets

CANNULA HAVING NITINOL REINFORCED INFLOW REGION

CROSS-REFERENCE TO RELATED APPLICATIONS

This application is a divisional of U.S. patent application Ser. No. 15/463,156, filed Mar. 20, 2017 (now allowed). The specification of the foregoing application is hereby incorporated by reference in its entirety.

BACKGROUND

A heart pump, such as a percutaneous intracardiac heart pump assembly, can be introduced in the heart to deliver blood from the heart into an artery. When deployed in the heart, a heart pump assembly pulls blood from the left ventricle and expels the blood into the aorta, or pulls blood from the right ventricle and expels blood into the pulmonary artery. Some heart pump assemblies pull blood through inflow apertures into a cannula and expel the blood from the cannula through outflow apertures.

Inflow apertures are traditionally formed of stainless-steel. They may include edges that can damage the blood as it enters the cannula, causing hemolysis. Furthermore, stainless steel portions are stiff and can be damaged by applied stresses, for example, during manufacturing, shipment, and/or when the device is being inserted into the body. During insertion, for example, the heart pump can be inadvertently damaged by the user grasping the sides of the inflow cage near the inflow apertures, deforming the cage. Accordingly, there is an opportunity for improved cannula designs.

SUMMARY

Systems, devices, and methods described herein provide heart pump assemblies with inflow apertures reinforced by a shape memory material. The reinforced inflow apertures are designed to prevent or reduce damage to the pump during insertion of the pump into position in the body and damage to blood during operation of the pump. In particular, the reinforced inflow aperture portion can withstand the stress of squeezing or bending and return to an original shape after exposure to such stress, helping the inflow holes remain open. This ability to return to shape can decrease the occurrence of inadvertent damage to blood pumps during insertion. The reinforced inflow apertures formed in a shape memory material portion of a heart pump can be embedded in a plastic cannula, and edges of the inflow apertures can be coated with a plastic coating, providing a more smooth surface for blood to pass than in prior art systems.

Several advantages can be achieved by the designs disclosed herein. For example, embedding nitinol in a coil or sheet to reinforce the cannula body and inflow section of the pump allows the miniaturization of the heart pump assembly for use in the heart. The reinforced inflow holes and cannula decrease the potential for damage to the heart or blood during use. Further, reinforced inflow holes which expose only the cannula body material to blood and tissues allow the pump to be positioned across the aortic valve without damage to the tissues. Nitinol can be manufactured to be thinner than other commonly used biocompatible materials such as stainless steel, and is more flexible for easier use and handling.

In one aspect, an intravascular heart pump assembly includes an elongate catheter with a proximal end to be positioned outside of a patient's body and a distal end to be positioned in an artery proximate to that patient's heart, a rotor with at least one impeller blade coupled to the distal end of the elongate catheter, a motor operatively coupled to the rotor, and a cannula. The cannula includes a cannula body having a proximal region including a proximal end and a distal region including a distal end, the proximal end coupled to the distal end of the elongate catheter. The cannula body has a proximal region and a distal region, with the distal region including at least one lateral inflow hole and the proximal region including at least one lateral outflow hole. The cannula also includes a sheet formed of a shape memory material and embedded within polymer, the sheet and the polymer forming the cannula body. In the distal region of the cannula body, the at least one lateral inflow hole is defined by a first layer having a hole in the shape memory material sheet, and by a second layer having a hole in the polymer material, and the hole in the first layer and the hole in the second layer overlap along an external surface of the cannula.

In some embodiments, an outer perimeter of the hole in the second layer is within an outer perimeter of the hole in the first layer. In some embodiments, the heart pump assembly also includes at least one slitted opening in the sheet configured to allow the sheet to flex. In some embodiments, the cannula body also includes a coil formed of a shape memory material. In some implementations, at least a portion of the coil is positioned proximal to the shape memory material sheet. In some implementations, at least a portion of the coil is positioned distal to the shape memory material sheet.

In some embodiments, the shape memory material is nitinol. In some embodiments, the cannula body is formed of two polymer layers with the nitinol (or other shape memory material) sheet embedded between the two polymer layers.

In some embodiments, the at least one lateral outflow hole is proximal to or aligned with the rotor. In some embodiments, the proximal region including the at least one lateral outflow hole is formed from a non-memory alloy with a plurality of lateral outflow holes. In some embodiments, the proximal region including the at least one lateral outflow hole is formed from stainless steel. In some embodiments, the heart pump assembly includes a flexible projection coupled to a distal end of the cannula. In some embodiments, the distal projection is a pigtail extension.

In some embodiments, the distal region of the cannula body includes a plurality of lateral inflow holes reinforced according to any of the embodiments discussed herein. In some embodiments, the distal region includes a second lateral inflow hole positioned proximal to the at least one first lateral inflow hole. In some embodiments, the cannula body has an outer diameter less than or equal to about 22 Fr (e.g., 12 Fr or 20 Fr). In some embodiments, the shape memory material sheet is less than or equal to about 0.07 mm thick. In some embodiments, a wall of the cannula body is at least 0.07 mm thick.

In another aspect, a method for producing a blood pump includes making a cannula with a reinforced inflow section. In some applications, the method includes providing a cannula body, producing a blood inflow section by forming a first plurality of apertures and a plurality of slits in a shape memory material sheet, rolling the shape memory material sheet into a cylindrical shape, embedding the shape memory material sheet in the cannula body, and forming a second plurality of apertures through the cannula body, wherein each of the first plurality of apertures and the second plurality of apertures fully overlap.

In some embodiments, the second plurality of apertures is formed such that an outer perimeter of each of the second plurality of apertures is within an outer perimeter of one of the first plurality of apertures. In some embodiments, the shape memory material is formed of nitinol. In some embodiments, embedding the shape memory material sheet in a plastic material comprising the cannula body includes placing the shape memory material sheet between a first polymer layer and a second polymer layer, and forming holes in the first and second polymer layers to coincide with holes in the shape memory material sheet.

Variations and modifications will occur to those of skill in the art after reviewing this disclosure. The disclosed features may be implemented in any combination and subcombination (including multiple dependent combinations and subcombinations), with one or more other features described herein. For example, although various specific arrangements of apertures are described herein, a heart pump assembly may be configured to have any number of apertures arranged in any suitable number or organization of rings. Further, the apertures may have any suitable size, shape, or position. The slitted holes formed in the shape memory material sheet to allow bending and/or flexing of the cannula may also be formed in any suitable orientation and arrangement with respect to inflow apertures. Sections of shape memory material wire coil can be positioned proximal and/or distal of the shape memory material sheet, or in some implementations may be omitted. The various features described or illustrated above, including any components thereof, may be combined or integrated in other systems. Moreover, certain features may be omitted or not implemented.

BRIEF DESCRIPTION OF THE DRAWINGS

The foregoing and other objects and advantages will be apparent upon consideration of the following detailed description, taken in conjunction with the accompanying drawings, in which like reference characters refer to like parts throughout, and in which.

DETAILED DESCRIPTION

Figure 1A:
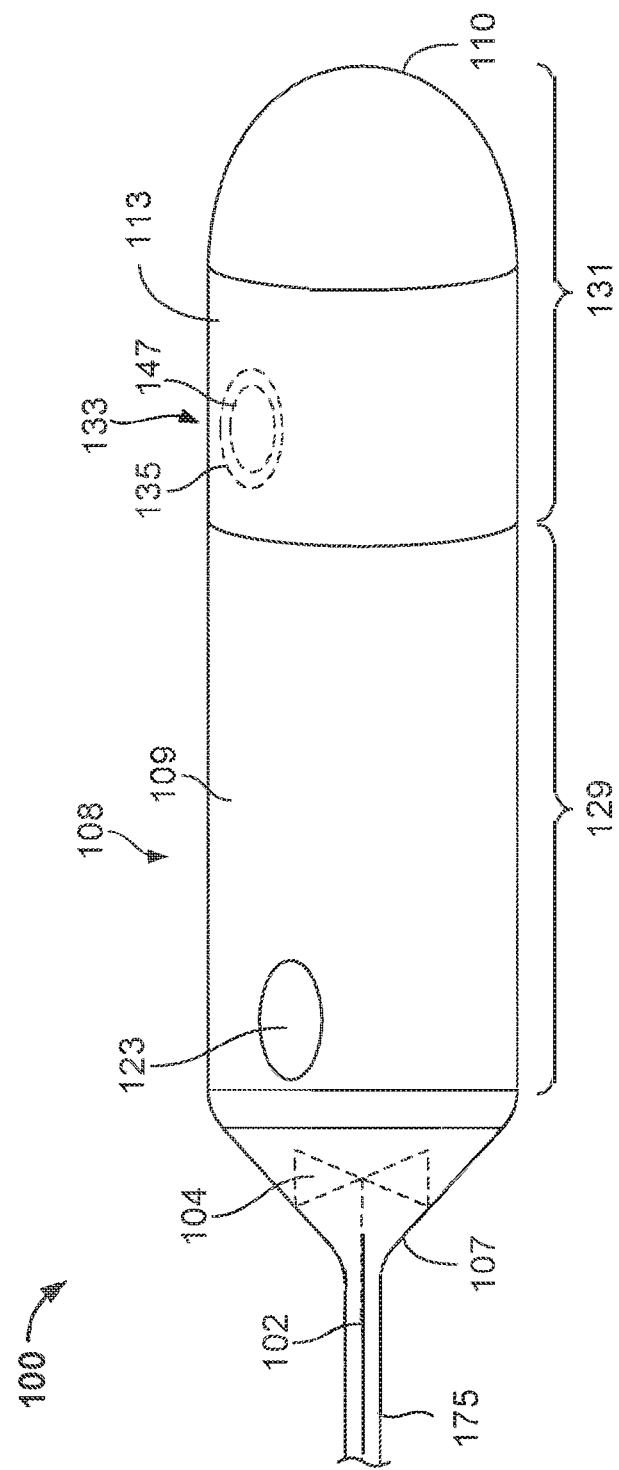
FIG. 1A shows a heart pump assembly including a shape memory material sheet.

To provide an overall understanding of the systems, methods, and devices described herein, certain illustrative embodiments will be described. Although the embodiments and features described herein are described with reference to specific numbers, sizes, and shapes of apertures, it will be understood that the heart pump assembly may be configured to have any suitable number of apertures formed in the inflow section, not limited to the arrangements described here. Additionally, the apertures may have any suitable size, shape, or position. It will also be understood that although the distal section of the cannula assembly is referred to as the "inflow" section, in case the blood flow direction is reversed as in a pump for supporting the right side of a patient's heart, this section would become an "outflow" section. As will be appreciated, all embodiments described herein are applicable for both left and right sided heart pumps.

Systems, devices, and methods described herein provide heart pump assemblies including a cannula with an improved inflow section. The reinforced inflow apertures prevent trauma to blood that enters the cannula through one or more inflow apertures. In particular, the inflow apertures are formed in a shape memory sheet embedded in the cannula such that blood entering the cannula does not contact sharp edges within the aperture, but only contacts the smooth cannula material (e.g., polymer) in which the shape memory sheet is embedded. Embedding a shape memory material sheet in a polymer material decreases potential damage to the blood, heart and other tissues, and allows miniaturization of the heart pump assembly for use in the heart. Furthermore, shape memory materials, such as nitinol, can be manufactured to be thinner than other commonly used biocompatible materials such as stainless steel, allowing the pump size to be decreased. During insertion, the pump can be subject to squeezing forces that may damage the delicate structures near the inflow apertures if the inflow section is rigid (e.g., if it made of non-flexible material such as stainless steel). If a pump is damaged during insertion, it may decrease pump efficiency or cause damage to blood and tissue. The shape memory material sheet imparts flexibility at the inflow section and may also decrease the risk of damage to the inflow section during insertion of the pump into the introducer.

The heart pump includes a cannula body with a shape memory material sheet forming an inflow section. For example, the sheet can be formed as an inflow cage/basket. The inflow section includes at least one first hole formed in the shape memory material sheet, e.g., in the inflow basket. The shape memory material sheet is embedded in a material of the cannula body, and a second hole is formed in the cannula body material overlapping with the first hole in the sheet to permit blood entering the cannula to pass through the holes without damage. The second hole in the cannula body material may be of a smaller diameter than the concentric first hole in the sheet, such that blood and tissues interact only with the edges of the second hole, i.e., with edges of the inflow aperture formed from the cannula body material. The cannula body may be formed from a material which does not damage blood or tissue. Furthermore, the cannula body may comprise a polymer coated section extending from the pump section at a proximal end of the cannula body to the distal end of the cannula. A shape memory material coil may also be applied. For example a nitinol coil may be embedded within the cannula body to reinforce the cannula body over a portion of the cannula. The shape memory material coil also enables the cannula to flex and bend during insertion and to return to its original shape. And further, the shape memory material coil can be positioned proximal or distal of the basket. The use of a memory shape material sheet (and coil where used) increases the flexibility of the pump and allows the pump to retain its shape if it is subjected to squeezing forces during insertion into the body or into an introducer device.

FIG. 1A shows an example heart pump assembly 100 including a shape memory material sheet 113 formed as an inflow cage/basket. The heart pump assembly has a proximal end 107 coupled to an elongate catheter 175, and a distal end 110, as well as a cannula 108, with cannula body 109, and a rotor 102 having an impeller blade 104. The cannula body 109 includes a first distal region 131 and a second proximal region 129. The first distal region 131 includes a shape memory material sheet 113 formed as a cylindrical inflow cage/basket embedded within a polymer, with a first lateral hole 133 formed in it. The second proximal region 129 includes a second lateral hole 123. The first lateral hole 133 is defined by a first hole 135 formed in the shape memory material sheet 113 and a second hole 147 in the polymer, which overlap.

The shape memory material sheet 113 is embedded in the cannula body 109 material, such that the shape memory material sheet 113 provides reinforcement of an inflow section of the cannula 108, but is not exposed to blood or tissue. The first lateral hole 133 is formed such that blood and tissue are protected from contacting sharp edges of the shape memory material sheet 113. The first hole 135 and the second hole 147 defining the first lateral hole 133 fully overlap as shown. For example, the second hole 147 is formed within the first hole 135. Blood flowing through the vasculature of a patient in the direction from the distal end 110 to the proximal end 107 of the cannula 108 flows into the cannula body 109 through the first lateral hole 133 which functions as an inflow aperture. Blood enters the cannula body 109 at an angle such that if the blood comes into contact with an edge of the first lateral hole 133, it is likely to be in contact with an edge of the hole formed in the cannula body 109 material. In some implementations, the first hole 135 and the second hole 147 may be entirely concentric, and the second hole 147 through the cannula body 109 is the same size or smaller than the first hole 135. In this way, the edges that define the first lateral hole 133 are formed from the cannula body 109 material, and the material of the shape memory material sheet 113 is not exposed.

Figure 1B:
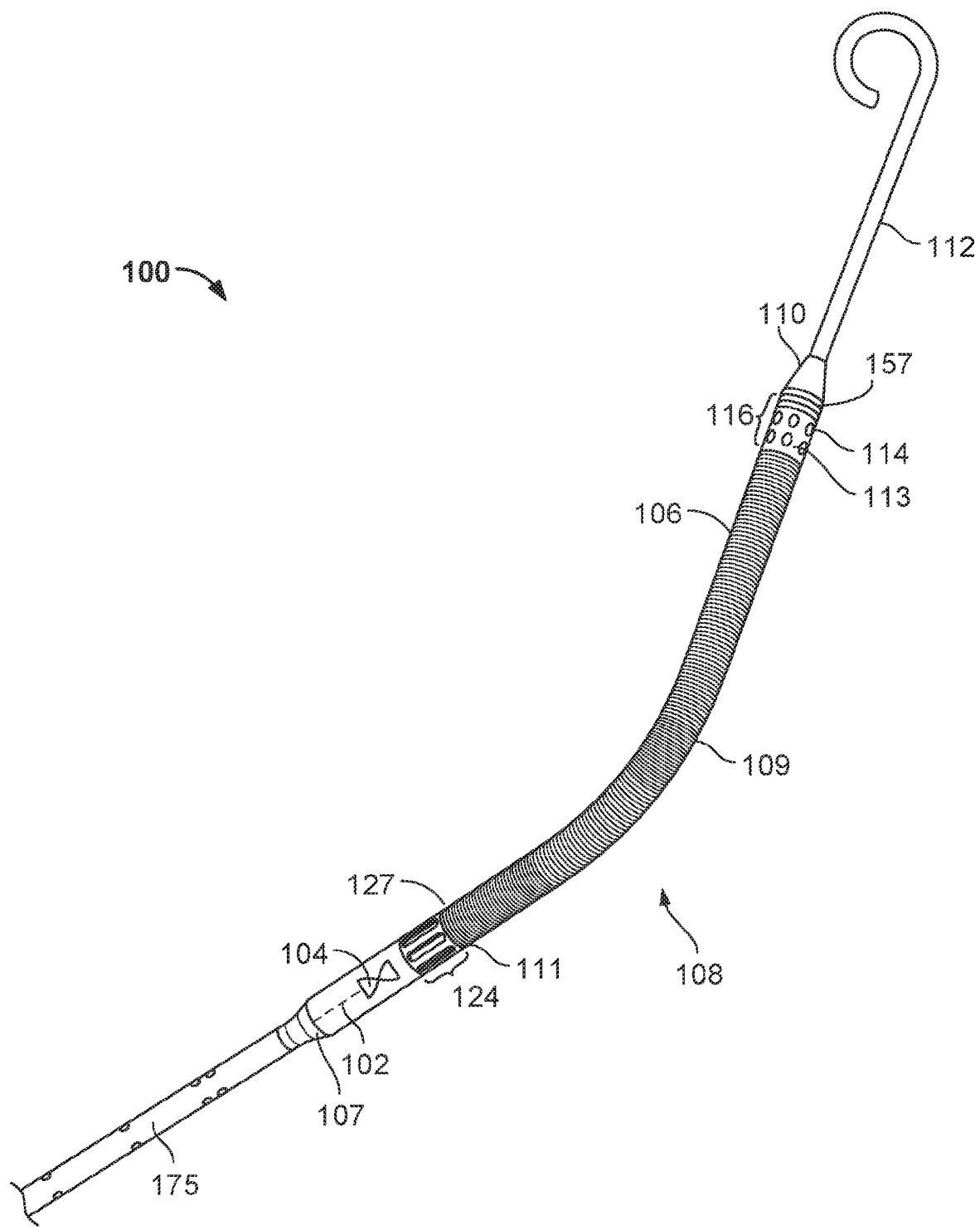
FIG. 1B shows a heart pump assembly including an inflow section and coil.

FIG. 1B shows a more detailed view of the heart pump assembly 100 of FIG. 1A, including a shape memory material sheet 113 and coil 106. The heart pump assembly 100 includes a catheter 175, a rotor 102, a cannula 108, an inflow section 116, an outflow section 124, outflow apertures 127, a proximal end of the pump 107, a distal end of the pump 110, and an atraumatic tip 112. The cannula 108 has a proximal end 111, a cannula body 109, and a distal end 157. A coil 106 is embedded in the cannula body 109. The coil 106 extends from the outflow section 124 at the proximal end 111 to the inflow section 116. The inflow section 116 is formed of at least one lateral hole 114 in a shape memory material sheet 113 embedded in the cannula body 109. The rotor 102 includes an impeller blade 104.

The rotor 102 is coupled to a distal end of the catheter 175, and is operatively coupled to a motor (not shown). The heart pump assembly 100 pulls blood through the at least one lateral inflow hole 114 in the distal inflow section 116 and into a lumen (not shown) in the cannula body 109. The blood is expelled through the outflow section 124 at the plurality of outflow apertures 127. The at least one lateral hole 114 is defined by overlapping holes formed in the shape memory material sheet 113 and in the cannula body 109 material (as shown in FIG. 1A). The blood enters the cannula 108 through the at least one lateral hole 114 and may contact the edge of the at least one lateral hole 114 as it enters. Blood cells may become damaged if they come into contact with sharp edges at high flow rates. The inflow section 116 formed in the shape memory material sheet 113 is embedded in the cannula body 109 material in order to present only the smooth cannula body 109 material to the blood as it enters through the at least one inflow hole 114 into the cannula body 109, protecting the blood from damage. After entering the cannula body 109, the blood flows through the cannula 108 and is expelled at the proximal end of the cannula 108 through the outflow apertures 127 at the outflow section 124. The outflow apertures 127 may be arranged laterally about the cannula body 109 such that at least one outflow aperture 127 is proximal to or aligned with the rotor 102. In case of blood flow direction reversal, the description above still holds, but outflow section 124 would act as the inflow and inflow section 116 would act as an outflow.

The heart pump assembly 100 may be percutaneously inserted into the heart and into the aorta. The inflow section 116 may be positioned past the aortic valve in the left ventricle, in order to pull blood from the left ventricle and expel the blood into the aorta. Extending the cannula 108 from the outflow section 124 to the sheet 113 embedded in the cannula body 109 such that the cannula wall is a smooth surface which eliminates occurrence of hemolysis or tissue damage in the aortic valves and vasculature. The at least one lateral hole 114 formed in the sheet 113 in the inflow section 116 embedded in the cannula body 109 can be reinforced at the edges by the smooth material of the cannula body 109 to decrease damage (e.g., hemolysis) to the blood. Atraumatic tip 112 also decreases damage to the heart tissues by spacing the heart pump assembly 100 from the heart walls. In some instances the at least one lateral hole 114 of inflow section 116 may be positioned near to the walls of the heart or various heart structures, such as the leaflets of the mitral valve. The cannula body 109 material in which the sheet 113 is embedded serves to soften the edges of the at least one lateral hole 114 to decrease damage to these structures if they are pulled toward the at least one lateral hole 114 by the suction of the pump.

Figure 2:
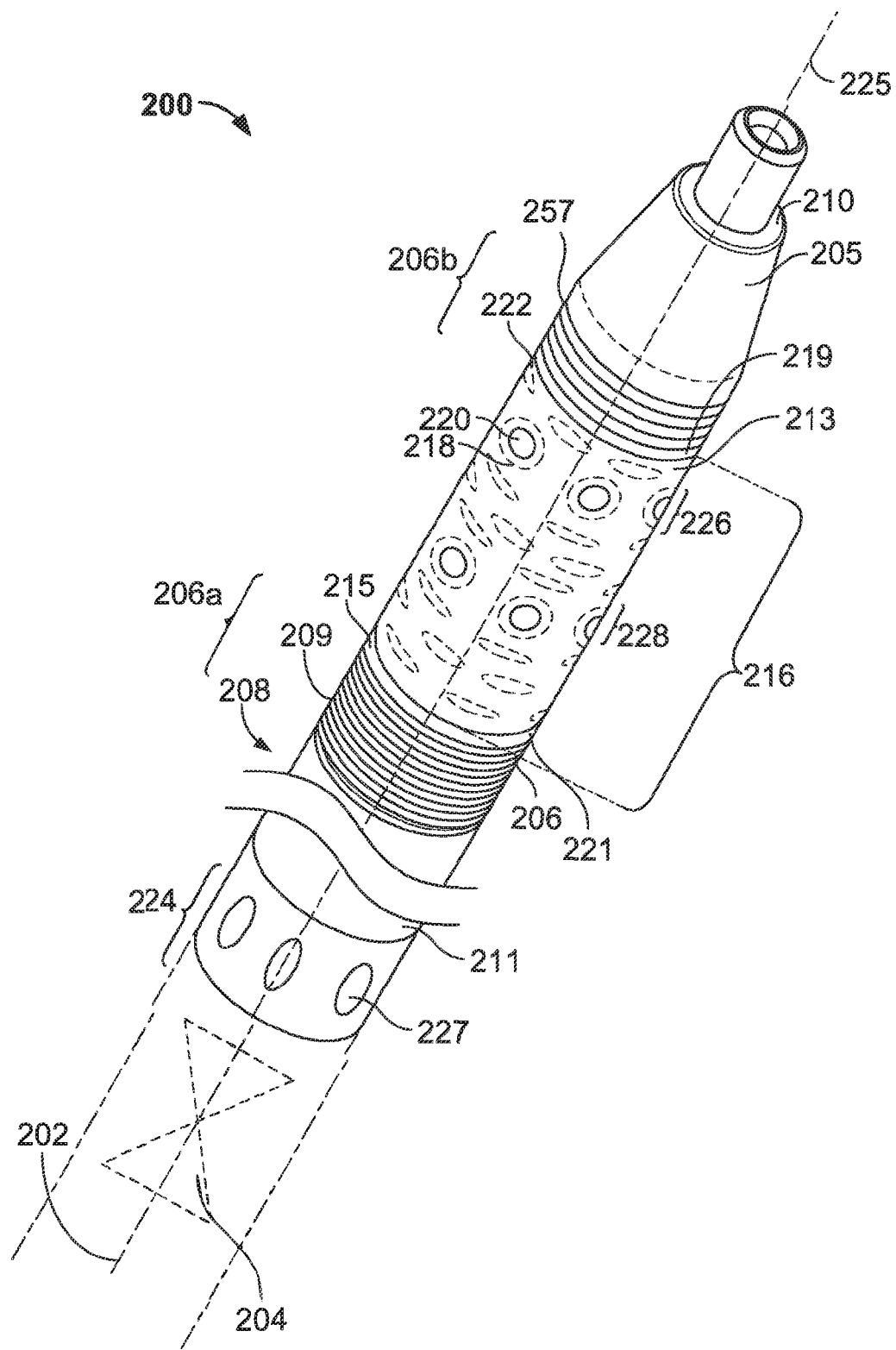
FIG. 2 shows a heart pump assembly including a plurality of apertures in an inflow section, according to one embodiment.

The basic configuration of FIGS. 1A and 1B may be implemented in any of the embodiments discussed herein. FIGS. 2-5 show various example patterns with which the configuration of FIGS. 1A and 1B can be implemented. Further example patterns showing arrangements of apertures in a wall of the cannula forming an inflow section are described in U.S. provisional application 62/382,471, the contents of which are incorporated by reference herein. FIG. 2 shows a heart pump assembly 200 having a reinforced inflow section 216, according to certain embodiments. The reinforced inflow section 216 is configured as a cage/basket and fitted within the heart pump assembly 200. The heart pump assembly 200 includes a rotor 202, an impeller blade 204, a cannula 208 (with proximal 211 and distal 257 ends), a cannula body 209, an outflow section 224, a plurality of outlets 227, and a distal connector 205. The assembly has a longitudinal axis 225 and a distal end 210. A coil 206 may have two coil sections 206a and 206b and is embedded in the cannula body 209. The inflow section 216 is positioned in this case between coil sections 206a and 206b and includes a reinforcing sheet 213 embedded in the cannula body 209. The sheet 213 includes a proximal sheet end 221 and a distal sheet end 219. A first row of holes 226 and a second row of holes 228 are formed in the embedded sheet 213. At least one slitted hole 222 is also formed in the embedded sheet 213 to enable the sheet to easily bend during insertion and positioning.

The second row of holes 228 is proximal of the first row of holes 226. The first row of holes 226 and second row of holes 228 may be formed so as to extend through both the embedded sheet 213 and the cannula body 209, such that the first row of holes 226 and second row of holes 228 allow blood to enter the cannula 208. For example, a first hole 218 is formed through the sheet 213 and a concentric second hole 220 is formed through the cannula body 209. The first hole 218 is shown as being larger than the second hole 220, such that blood entering the cannula 208 interacts only with smooth edges of the second hole 220 in the cannula body 209 and not with sharp edges of the first hole 218 formed in the shape memory sheet 213. Each aperture of the first row of holes 226 and the second row of holes 228 can be aligned along the longitudinal axis 225 of the cannula 209, or may be offset from one another. The at least one slitted hole 222 may be formed only in the sheet and embedded in the cannula body 209, such that it does not provide an aperture through which blood enters the cannula 208. Instead, the at least one slitted hole 222 may allow the sheet 213 to flex or bend, for example during insertion into an introducer sheath or during positioning within a patient's body. The at least one slitted hole 222 may be oriented to allow bending or flexing in a preferred direction.

The coil section 206 can be provided at a desired length. For example, the coil section 206a may be 15-20 cm (e.g., 13 cm, 15 cm, 17 cm, 19 cm, 20 cm, 22 cm, or 24 cm). The coil 206 (sections 206a and 206b) embedded in the cannula body 209 may extend from the outflow section 224 to the proximal sheet end 221. The coil 206 may also extend from a distal sheet end 219 to the distal connector 205. The outflow section 224 includes one or more apertures 227. The coil 206 may be joined to the sheet 213. Alternatively, the coil 206 and sheet 213 may be unconnected except by being embedded in the cannula body 209. In that arrangement, the coil 206 would reinforce the cannula body 209, while the sheet 213 would reinforce the apertures in the inflow section 216.

In some implementations, the sheet 213 is formed from a shape memory material. In some implementations, the shape memory material forming the sheet 213 is principally constructed of nitinol. In some implementations, the coil 206 also is formed from a shape memory material. In some implementations, shape memory material forming the coil 206 is principally constructed of nitinol. A coil 206 and/or sheet 213 formed from nitinol or another shape memory material allows flexibility of the cannula 208 during introduction into an introducer or positioning in the body. For example, in some implementations the inflow section 216 may experience substantial force when gripped and squeezed during introduction of the pump 200 into an introducer sheath or catheter. A cannula 208 and inflow section 216 formed of a shape memory material can withstand the squeezing force and resume its original shape after the force has stopped. This can decrease damage to the pump during introduction. The coil 206 further allows flexibility of the cannula body 209. In some implementations, the cannula body 209 is formed of a biocompatible plastic material (e.g., polyurethane). Embedding the shape memory material coil 206 and sheet 213 in the cannula body 209 reinforces the cannula body 209 and the holes (for example, first row of holes 226 and the second row of holes 228) while exposing only the cannula body 209 material to the tissue and blood of the patient.

The cannula 208 extends from proximal end 211 distal of the outflow section 224 to the distal end 257 where the cannula body 209 is coupled to the distal connector 205. The cannula 208 includes the cage/basket of the inflow section 216. The cannula 208 may have an external surface coated by a polymer layer to present a smooth surface that does not damage blood as it enters or passes by the cannula 208. It will be appreciated that though the cannula 208 in FIG. 2 includes a first section of coil 206a, an inflow section 216 including a shape memory material sheet, and a second section of coil 206b, the cannula 208 does not require two coil sections and in fact in some embodiments includes no coil-reinforced sections.

Several advantages can be achieved by the designs disclosed herein. For example, embedding a nitinol coil 206 and sheet 213 to reinforce the cannula body 209 and inflow section 216 of the pump allows the miniaturization of the heart pump assembly 200 for use in the heart. The reinforced holes (i.e., first row of holes 226 and second row of holes 228) and cannula 208 decrease the potential for damage to the heart or blood during use. Further, reinforced holes which expose only the cannula body material to blood and tissues allow the pump to be positioned across the aortic valve without damage to the tissues. Nitinol can be manufactured to be thinner than other commonly used biocompatible materials such as stainless steel, and is more flexible for easier use and handling.

Figure 3:
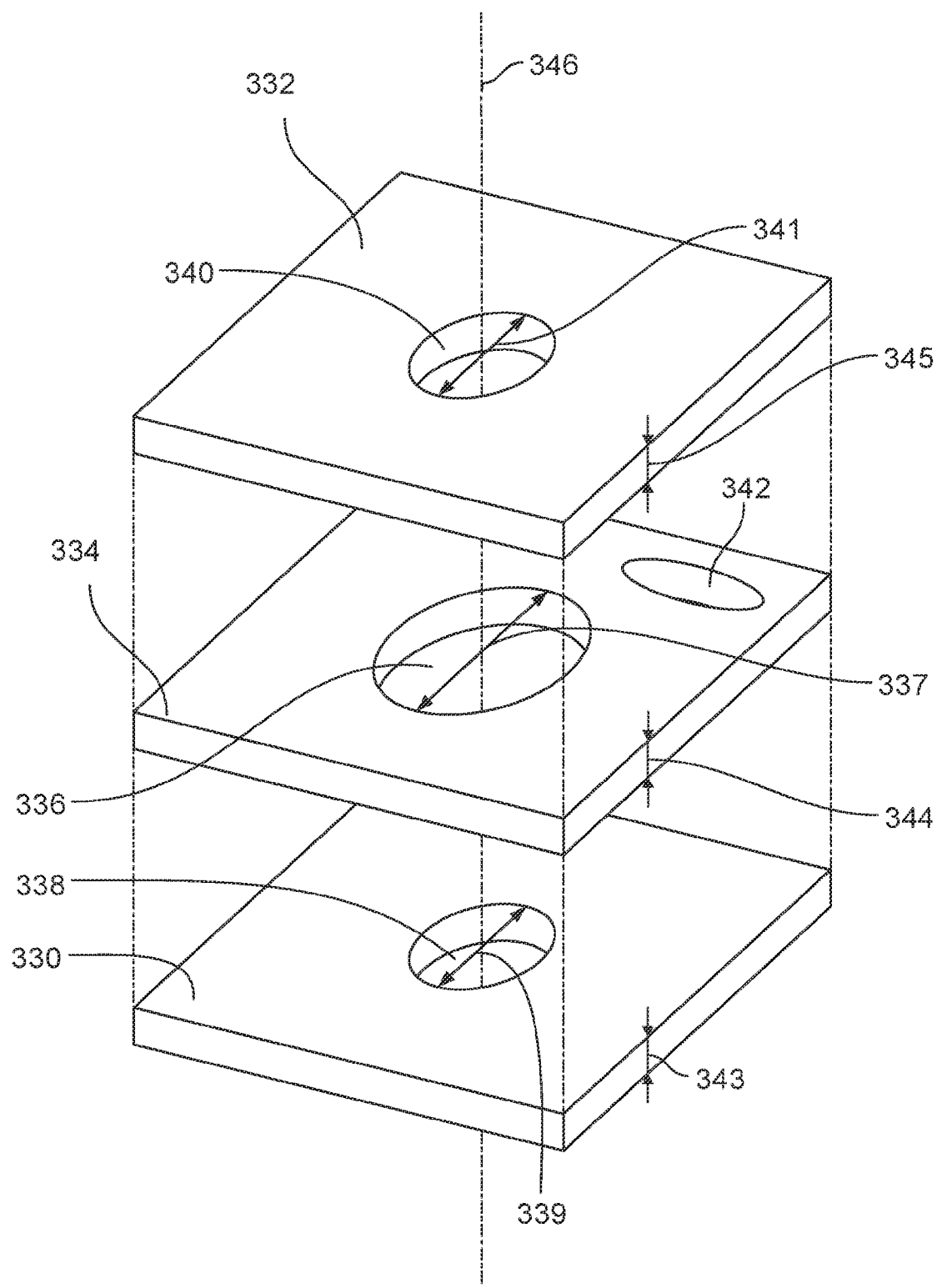
FIG. 3 shows layers of polymer material and shape memory alloy making up the cannula body, in accordance with example implementations.

FIG. 3 shows an illustrative view of a multilayered inflow section of the heart pump assembly, such as heart pump assembly 100 in FIG. 1A or FIG. 1B, or 200 in FIG. 2, according to some implementations. Embedding a reinforcing sheet between two layers of plastic coating ensures that blood entering the cannula through the holes in the reinforced section will encounter only the smooth edges of the plastic coating and not sharp edges of the reinforcing sheet. The inflow section (such as inflow section 116 in FIG. 1 or 216 in FIG. 2) includes a layer of nitinol 334, a first layer of plastic 330, a second layer of plastic 332, and an axis 346 perpendicular to each of the layers. The layer of nitinol 334 includes a first aperture 336 with a first diameter 337, a slitted hole 342, and a first thickness 344. The first layer of plastic 330 has a second aperture 338 with a second diameter 339, and has a second thickness 343. The second layer of plastic 332 has a third aperture 340 with a third diameter 341, and has a third thickness 345. The layer of nitinol 334 is embedded between the first layer of plastic 330 and the second layer of plastic 332. The first aperture 336, second aperture 338, and third aperture 340 are aligned along the axis perpendicular to each of the three layers, such that the apertures overlap to create a through hole for blood to flow into the cannula. The apertures may overlap entirely, as shown, such that the first aperture 336, second aperture 338, and third aperture 340 are concentric. In some embodiments, the first aperture 336, second aperture 338, and third aperture 340 alternatively overlap only in portion. The first diameter 337 in the first aperture 336 in the first layer of nitinol 334 is larger than the second diameter 339 of the second aperture 338 and the third diameter 341 of the third aperture 340. The smaller second diameter 339 and third diameter 341 allow only the material of the first plastic layer 330 and second plastic layer 332 to be exposed to blood entering the cannula, keeping the blood from being damaged by sharper edges in the layer of nitinol 334.

Coating the shape memory alloy sheet on an outside portion of the cannula protects blood from being damaged by sharp edges. Coating the shape memory alloy sheet on an interior portion of the cannula similarly protects the blood and may also help to maintain a consistent flow pattern as the blood moves through the cannula. In some implementations, the thickness 343 of the first layer of plastic 330 and the thickness 345 of the second layer of plastic 332 are approximately equal. In some implementations, the thickness 343 of the first layer of plastic 330 is greater than the thickness 345 of the second layer of plastic 332 The thickness of the shape memory material sheet enables the reinforced cannula to be bent or flexed but still maintain its shape. The total thickness of the cannula wall includes a thickness of the nitinol (or other shape memory material) and the thickness of the polymer in which the nitinol is embedded. In some implementations, the layer of nitinol 334 forming the shape memory material sheet is less than or equal to 0.07 mm in thickness. In some implementations, the layer of nitinol 334 forming the shape memory material sheet is 0.03 mm, 0.05 mm, 0.07 mm, 0.09 mm, 0.1 mm, 0.2 mm, 0.25 mm or any suitable thickness. In some implementations, the combined height of the layer of nitinol 334, first layer of plastic 330 and second layer of plastic 332 is 0.05 mm, 0.07 mm, 0.09 mm, 0.1 mm, 0.2 mm, 0.25 mm, 0.3 mm, 0.5 mm or any suitable thickness. In some implementations, the thickness 343 of the first layer of plastic 330 is greater than the thickness 345 of the second layer of plastic 332 and is equal to 0.03 mm, 0.04 mm, 0.05 mm, 0.08 mm, 0.1 mm, or any other suitable thickness. In some implementations, the thickness required of the shape memory material sheet to withstand squeezing and bending forces during insertion may be less than a thickness that would be required of a non-shape memory material to withstand similar forces. The layers of shape memory material and plastic layers do not substantially increase a thickness of the cannula body wall as compared to the wire-reinforced cannula without the shape memory sheet.

In some implementations, the first layer of plastic 330 faces an interior of the cannula body. In some implementations, the second layer of plastic 332 faces an interior of a cannula body. In some implementations, an edge of the aperture 338 in the first plastic layer 330 and/or an edge of the aperture 340 in the second plastic layer 332 is rounded, beveled, or chamfered. In some implementations, the entirety of an edge of the first aperture 336 is embedded in the material of the first plastic layer 330 and the second plastic layer 332. In some implementations, the edge of the first aperture 336 is embedded in the material of the first plastic layer 330 and the second plastic layer 332. For example, a proximal edge of the first aperture 336 may be fully embedded in the material of the first plastic layer 330 and the second plastic layer 332 forming a smooth surface that prevents damage to blood entering the cannula.

The slitted hole 342 formed in the layer of nitinol 334 may be formed in any shape. The slitted hole 342 may be formed as an oblong slit which may be oriented to allow preferential bending or flexing of the cannula in a particular direction. The slitted hole 342 is formed in the layer of nitinol 334, but no corresponding aperture is formed in the first plastic layer 330 and the second plastic layer 332. Because of this, no blood enters the cannula through the slitted hole 342, but the slitted hole 342 serves to increase the flexibility of the cannula and allows bending and flexing of the cannula at the nitinol sheet.

In general, the reinforced inflow section embedded in the cannula body as shown in FIGS. 1A, 1B, and 2, can be constructed with holes arranged in any orientation. The slitted holes are added to the reinforcing sheet to allow the cannula to bend at the inflow section, enabling positioning of the cannula within the vasculature. The slitted holes may be produced to enable the inflow section to bend in particular directions to accommodate the bends required to position the cannula in a particular position within the heart. Alternatively, the slitted holes may be produced to enable the inflow section to withstand squeezing forces during insertion of the cannula, enabling the inflow section to be deformed and to resume the original shape without damage to the inflow holes. FIGS. 4-7 illustrate example arrangements of inflow holes and slitted holes to accomplish these outcomes.

Figure 4:
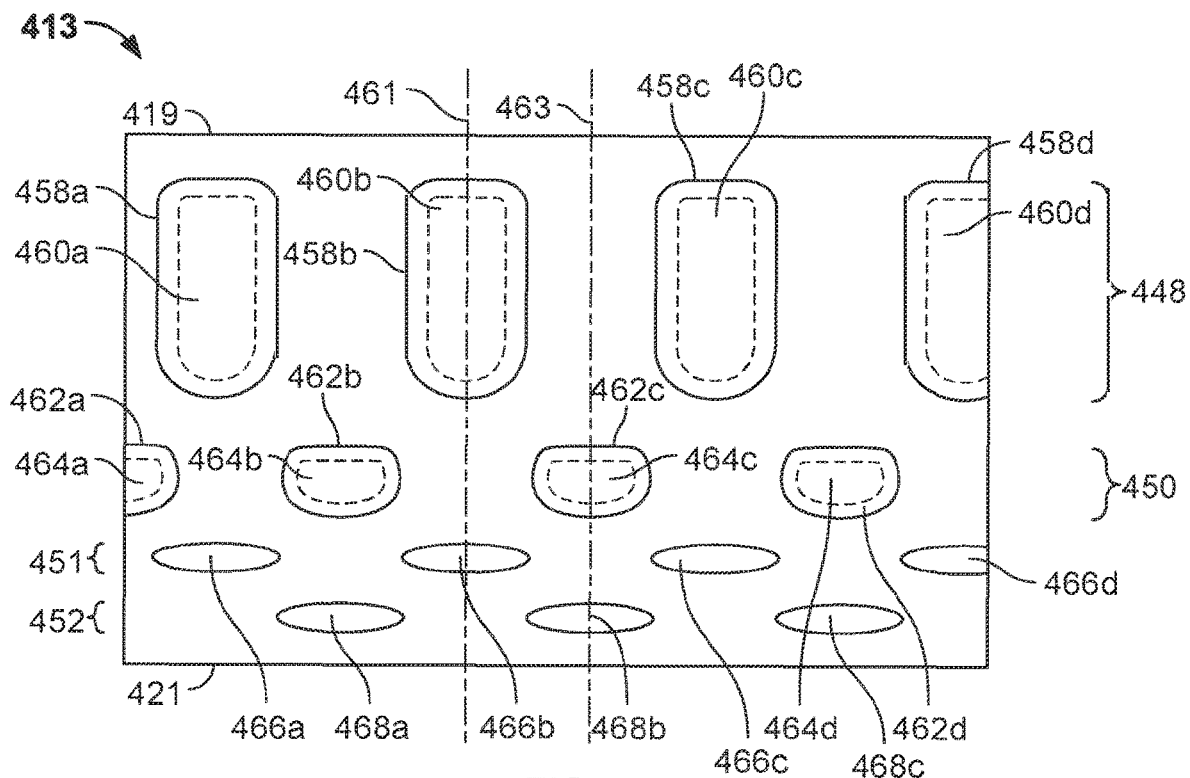
FIG. 4 shows an example pattern of apertures and slitted holes in a shape memory material sheet.

FIG. 4 shows a pattern of inflow apertures and slitted holes in a shape memory material sheet 413, in accordance with some implementations. Shape memory material sheet 413 (which can be coiled or rolled into a cage/basket formation and embedded within a cannula) includes a distal edge of the sheet 419, a proximal edge of the sheet 421, a first plurality of inflow apertures 448, a second plurality of inflow apertures 450, a first plurality of slitted holes 451 and a second plurality of slitted holes 452. The first plurality of inflow apertures 448 and the second plurality of inflow apertures 450 are formed as holes through the shape memory material sheet and covering cannula body material. In particular, apertures in the first plurality of inflow apertures 448 are formed from first aperture 458$a$-$d$ of the shape memory material sheet, and from second aperture 460$a$-$d$ of the cannula body material in which the shape memory material sheet is embedded. The first plurality of slitted holes 451 and the second plurality of slitted holes 452 are formed only in the shape memory material sheet 413.

The second plurality of inflow apertures 450 is proximal of the first plurality of inflow apertures 448. The first plurality of inflow apertures 448 and the second plurality of inflow apertures 450 may be offset from each other along an axis 461 running from a proximal edge of the sheet 421 to a distal end of the sheet 419. For example, aperture 460$b$ is offset from aperture 464$b$. The first plurality of inflow apertures 448 and the second plurality of inflow apertures 450 may be aligned with one or more of the holes in the first plurality of slitted holes 451 and a second plurality of slitted holes 452. For example, aperture 460$b$ is aligned with slitted hole 466$b$ along axis 461, and aperture 464$c$ is aligned with slitted hole 468$b$ along axis 463. Alignment of apertures with slitted holes allows the cannula to flex in a position proximal to the apertures allowing the inflow section to be deformed during positioning of the cannula, while maintaining sufficient rigidity and reinforcement of the apertures.

Though the first plurality of inflow apertures 448 and second plurality of inflow apertures 450 are defined by holes through the sheet 413 overlapping holes in the cannula body, the area of the holes is such that the flow rate of blood through the cannula is maintained. In some implementations, the first plurality of inflow apertures 448 may include apertures 460$a$-$d$ having a larger area than apertures 464$a$-$d$ of the second plurality of inflow apertures 450. The area of the apertures 460$a$-$d$ of the first plurality of inflow apertures 448 may be less than 20 mm$^2$. In some implementations, the area of apertures 460$a$-$d$ of the first plurality of inflow apertures 448 is 0.5 mm$^2$, 1 mm$^2$, 5 mm$^2$, 10 mm$^2$, 15 mm$^2$, 18 mm$^2$, 20 mm$^2$, 23 mm$^2$, 25 mm$^2$ or any other suitable area. The area of apertures 464$a$-$d$ of the second plurality of inflow apertures 450 may be less than 12 mm$^2$. In some implementations, the area of apertures 464$a$-$d$ of the second plurality of inflow apertures 450 may be 0.25 mm$^2$, 0.5 mm$^2$, 1 mm$^2$, 2 mm$^2$, 5 mm$^2$, 10 mm$^2$, 12 mm$^2$, or any other suitable area. The area of the apertures of the first plurality of inflow apertures 448 and the second plurality of inflow apertures 450 may be chosen to support a particular flow rate or flow pattern of blood into the cannula.

In some implementations, a large portion of blood that enters the cannula body enters through the most proximal of the plurality of apertures (e.g., the second plurality of inflow apertures 450), for example through the apertures 464a-d. Variations in the number and size of the apertures in the distal end portion can alter the flow distribution of blood into the cannula. All arrangements in FIGS. 4-6 show the plurality of apertures disposed on a similar portion of the distal end portion of the cannula (as shown in FIG. 1 A, 1B, or 2), but the apertures vary in the shape, positioning, and relative size.

Figure 5:
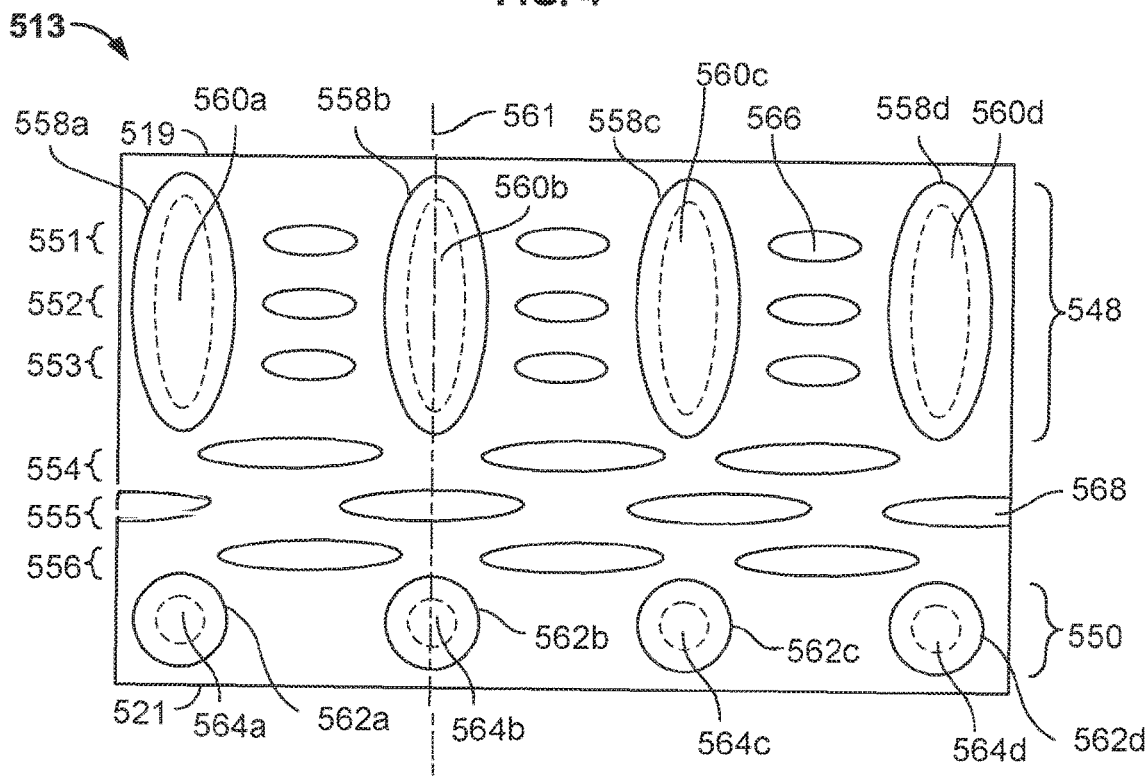
FIG. 5 shows another example pattern of apertures in a shape memory material sheet.

While FIG. 4 shows inflow apertures aligned with slitted holes in a shape memory material sheet, FIG. 5 shows a shape memory material sheet 513 having a pattern of inflow apertures with slitted holes set in between, in accordance with some implementations. The shape memory material sheet includes a distal edge 519, a proximal edge 521, a first plurality of inflow apertures 548, a second plurality of inflow apertures 550, a first plurality of slitted holes 551, a second plurality of slitted holes 552, a third plurality of slitted holes 553, a fourth plurality of slitted holes 554, a fifth plurality of slitted holes 555, and a sixth plurality of slitted holes 556. Apertures in the first plurality of inflow apertures 548 are formed from first apertures 558a-d formed in the shape memory material sheet and from second apertures 560a-d formed in the cannula body material in which the shape memory material sheet is embedded. Inflow apertures in the second plurality of inflow apertures 550 are formed from third apertures 562a-d formed in the shape memory material sheet and from fourth apertures 564a-d formed in the cannula body material.

The first plurality of inflow apertures 548 and the second plurality of inflow apertures 550 are aligned along an axis 561 running from a proximal edge of the sheet 521 to a distal end of the sheet 519. One or more of the slitted holes may also be aligned with the inflow apertures of the first plurality of inflow apertures 548 and the second plurality of inflow apertures 550. For example, aperture 560b and aperture 562b are aligned with a slitted hole of the plurality of slitted holes 555. Other slitted holes are interspersed between each of the first plurality of inflow apertures 548, for example, slitted holes of the first plurality of slitted holes 551, the second plurality of slitted holes 552, and the third plurality of slitted holes 553 are interspersed between the apertures 560a-d of the first plurality of inflow apertures 548. Interspersing slitted holes between the apertures of the first plurality of inflow apertures 548 increases the flexibility of the cannula and inflow section in the region of the apertures. This may prevent damage to the apertures during insertion of the cannula into an introducer sheath or into the vasculature of a patient. The increased flexibility of the inflow section in the region of the apertures may also assist in the placement of the cannula without damage to heart tissues.

Figure 6:
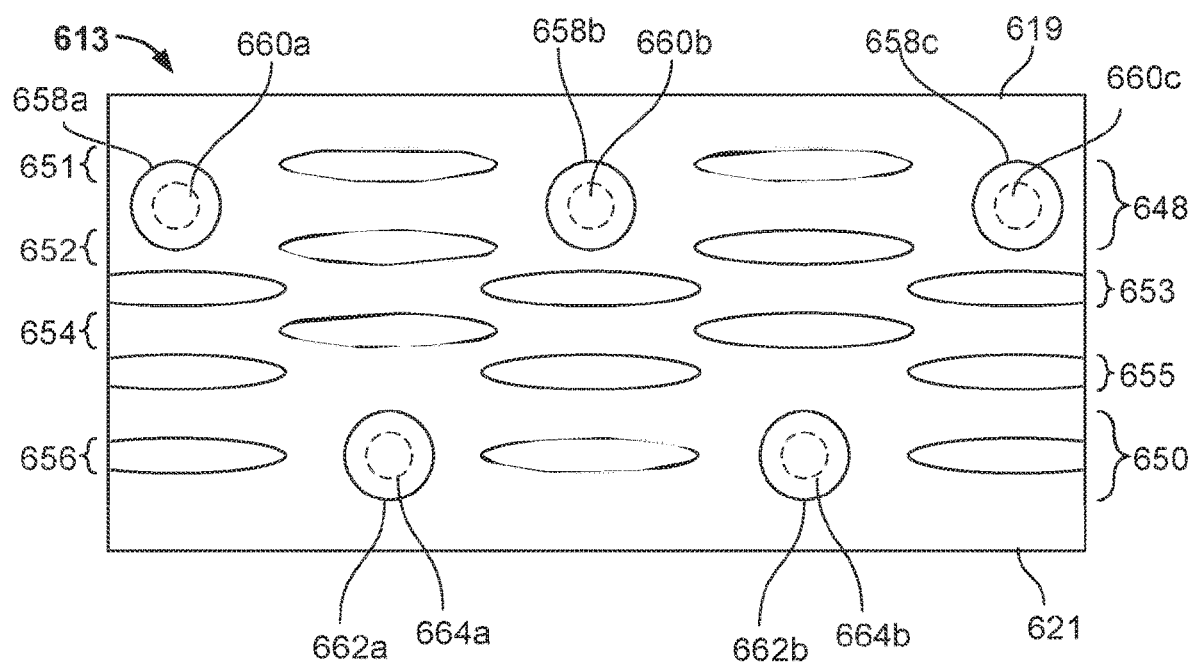
FIG. 6 shows yet another example pattern of apertures formed in a shape memory material sheet.

FIG. 6 shows a pattern of inflow apertures formed in a shape memory material sheet 613, in accordance with some implementations. Shape memory material sheet 613 includes a distal edge 619, a proximal edge 621, a first plurality of inflow apertures 648, a second plurality of inflow apertures 650, a first plurality of slitted holes 651, a second plurality of slitted holes 652, a third plurality of slitted holes 653, a fourth plurality of slitted holes 654, a fifth plurality of slitted holes 655, and a sixth plurality of slitted holes 656. Apertures in the first plurality of inflow apertures 648 are formed from first apertures 658a-d formed in the shape memory material sheet, and from second apertures 660a-d formed in the cannula body material in which the shape memory material sheet is embedded. Inflow apertures in the second plurality of inflow apertures 650 are formed from third apertures 662a and 662b formed in the shape memory material sheet, and from fourth apertures 664a and 664b formed in the cannula body.

In some implementations, the shape memory material sheet 613 is formed from a nitinol sheet. After the apertures and slitted holes (for example, first apertures 658a-c, third apertures 662a and 662b, first plurality of slitted holes 651, a second plurality of slitted holes 652, a third plurality of slitted holes 653, a fourth plurality of slitted holes 654, a fifth plurality of slitted holes 655, and a sixth plurality of slitted holes 656) are formed in the shape memory material sheet 613, shape memory second apertures 660a-c and fourth apertures 664a and 664b may be formed in the cannula body material to coincide with the apertures 658a-c and 662a-b. Alternatively, the shape memory material sheet 613 can be joined to the cannula, such as to a nitinol coil before being embedded in the material of the cannula body.

Figure 7:
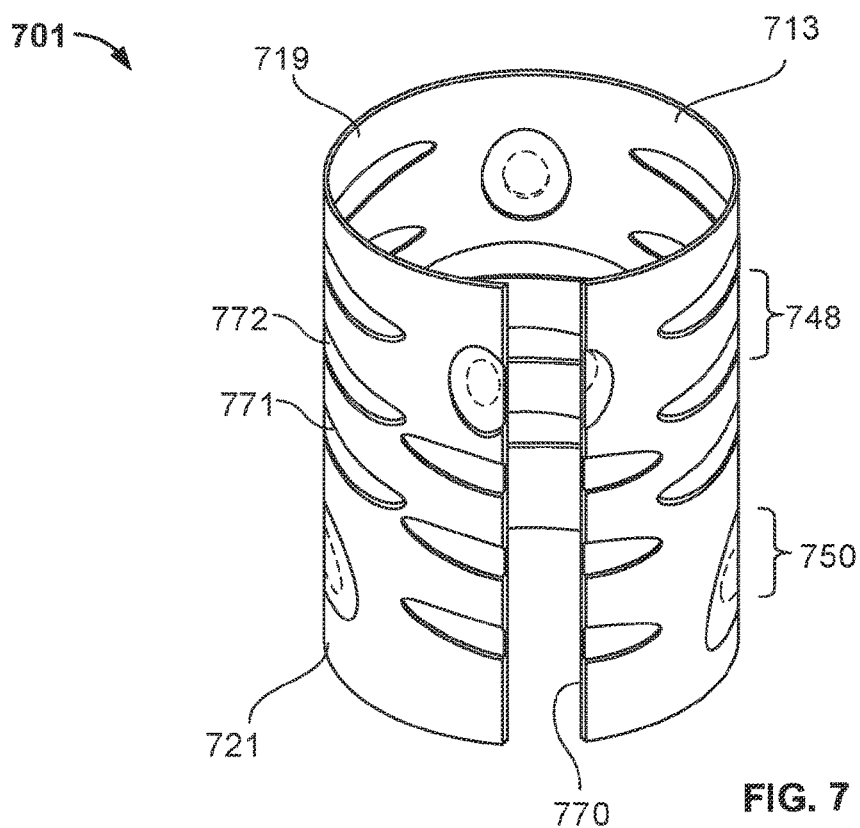
FIG. 7 shows a shape memory material sheet formed into a cylinder cage/basket, according to one embodiment.

FIG. 7 shows a shape memory material sheet (such as the memory material sheet 413 of FIG. 4, the memory material sheet 513 of FIG. 5, or the shape memory material sheet 613 of FIG. 6) formed into a cylinder 701 cage/basket. Cylinder 701 includes a shape memory material sheet 713, a distal end of the sheet 719, a proximal end of the sheet 721, a first plurality of inflow apertures 748, a second plurality of inflow apertures 750, and slitted holes 772 and slitted holes 771. The shape memory material sheet 713 is curved to form a cylinder such that each side edge of the memory material sheet 713 meets or approaches edge 770. The distal end of the sheet 719 and proximal end of the sheet 721 form the ends of the cylinder to which the shape memory coil may be attached.

Figure 8:
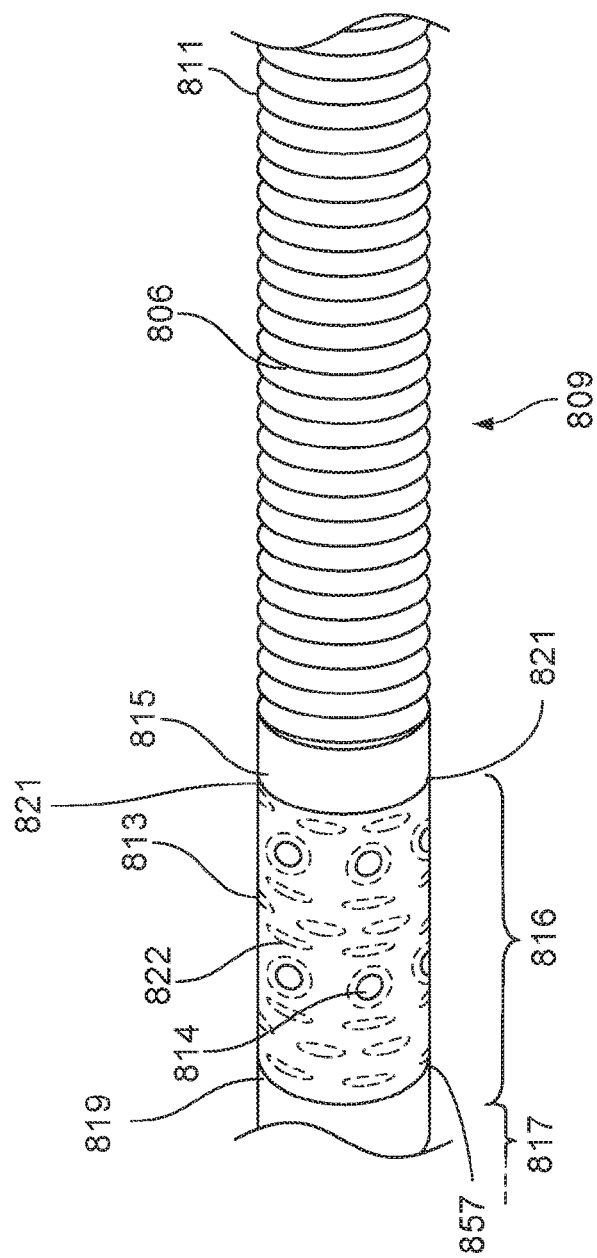
FIG. 8 shows a shape memory material sheet and a shape memory material coil embedded in a cannula body, according to one embodiment.

FIG. 8 shows a shape memory material sheet 813 and a shape memory material coil 806 embedded in a cannula body 809, in accordance with some implementations. Shape memory material sheet 813 includes an inflow section 816, at least one inflow aperture 814, at least one slitted hole 822, a distal end of the sheet 819 and a proximal end of the sheet 821. The cannula body 809 includes a coil 806, a proximal end of the cannula 811, and a distal end of the cannula body 857. The shape memory material sheet 813 is coupled to the coil 806 comprising the cannula body 809 at 815. The shape memory material sheet 813 is coupled at the distal end of the sheet 819 to a distal section 817 of the pump assembly. The distal section 817 may include an additional section of coil, such as coil 806. Alternatively or additionally, the distal section 817 may include an additional section of solid material, such as a section of stainless steel.

In some implementations, coil section 806 is joined to shape memory material sheet 813, forming a unitary shaped metal structure that stabilizes the cannula and openings. For example, the coil section 806 may be welded to the shape memory material sheet 813. In some implementations, coil section 806 and shape memory material sheet 849 are not joined but are embedded in the cannula body 809 material and therefore stabilize the cannula. Cannula body 809 may be formed of a plastic material such as polyurethane.

Figure 9:
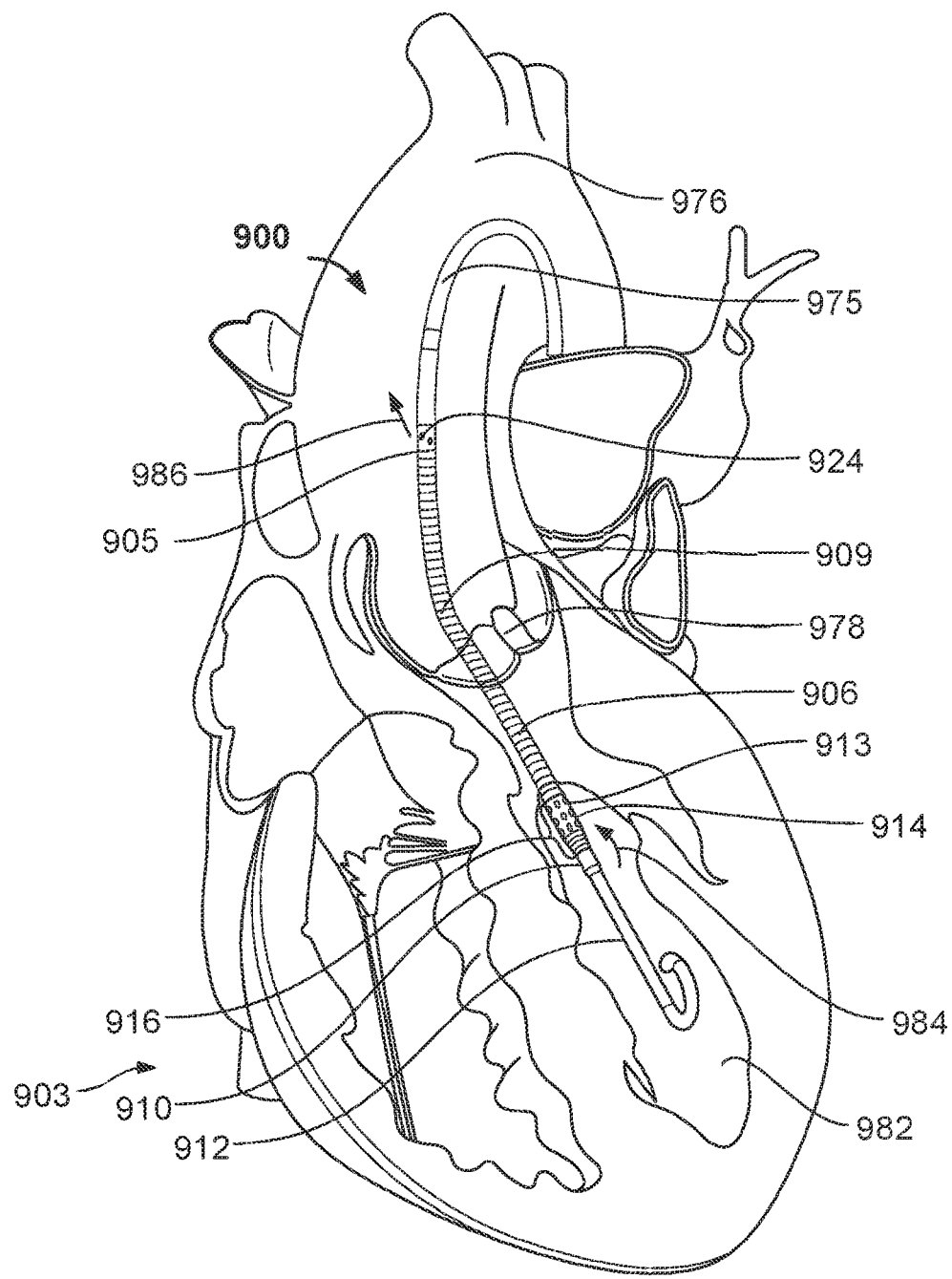
FIG. 9 shows an exemplary heart pump assembly including an inflow section inserted into a patient's heart.

FIG. 9 shows a heart pump assembly 900 located in a heart 903 of a patient. The heart 903 includes a left ventricle 982, aorta 976, and aortic valve 978. The heart pump assembly 900 includes a catheter 975, a motor housing 905, an outflow section 924, a cannula body 909, a coil 906, an inflow section 916, a shape memory material sheet 913, at least one inflow aperture 914 formed as a hole in the shape memory material sheet 913, a distal end of the cannula 910, and a flexible projection 912. The motor housing 905 is coupled at its proximal end to the catheter 975 and at its distal end to the cannula body 909. The motor 905 also drives a rotor (not visible in figure) which rotates to pump blood from the inflow section 916 through the cannula body 909 to the outflow section 924. Arrow 984 shows the direction of the blood as it enters the cannula body 909 at the inflow section 916, while arrow 986 shows the direction of the blood as it exits the cannula body 909 at the outflow section 924 into the aorta 976. The cannula body 909 is positioned across the aortic valve 978 such that the inflow section 916 is located within the left ventricle 982 and the outflow section 924 is located within the aorta 976. This configuration allows the heart pump assembly 900 to pump blood from the left ventricle 982 into the aorta 976 to support cardiac output. It will be appreciated that the pump 900 may be applicable as a left-side support device as shown, or may equally be used as a right-sided heart pump. In right-side support embodiments, the blood flow direction is reversed and the inflow section 916 will function as an outflow, and the outflow section 924 will function as an inflow.

The coil 906 and shape memory material sheet 913 increase the flexibility of the heart pump assembly 900, allowing it to be easily inserted into position in the heart 903. In some implementations, heart pump assembly 900 is first inserted into an introducer sheath (not shown). Insertion of the heart pump assembly 900 into a sheath may require a technician or health care professional to handle the heart pump assembly 900 and potentially to exert squeezing forces on various portions of the heart pump assembly 900. The shape memory material sheet 913 forming the inflow section 916 can withstand such squeezing forces and return to its intended shape even after being subjected to such forces. In some implementations, the outflow section 924 is formed from a non-memory material or alloy. For example, the outflow section 924 may be formed from stainless steel.

In some instances, the positioning of the heart pump assembly 900 places the inflow section 916 and the at least one inflow aperture 914 near valve leaflets or other heart tissues. This may be due to the individual anatomy of the particular heart 903. The walls or tissues of the heart 903 can be sucked by the suction of the pump towards the inflow section 916 and may become suctioned to the at least one inflow aperture 914, which may damage the tissues of the heart. Embedding the coil 906 and the shape memory material sheet 913 in the material of the cannula body 909 provides a pathway for blood to enter the cannula such that it encounters the smooth edges of the cannula body 909 material rather than sharp edges of the shape memory material sheet 913. Sharp edges of the shape memory material sheet 913 are embedded in the smooth cannula body 909 material, further protecting the heart tissues and leaflets from being damaged by sharp edges if the tissues are suctioned to an inflow aperture.

The heart pump assembly 900 pumps blood from the left ventricle into the aorta in parallel with the native cardiac output of the heart 903. The blood flow through a healthy heart is typically about 5 liters/minute, and the blood flow through the heart pump assembly 900 can be a similar or different flow rate. For example, the flow rate through the heart pump assembly 900 can be 0.5 liters/minute, 1 liter/minute, 1.5 liters per minute, 2 liters/minute, 2.5 liters/minute, 3 liters/minute, 3.5 liters/minute, 4 liters/minute, 4.5 liters/minute, 5 liters/minute, greater than 5 liters/minute or any other suitable flow rate.

The motor housing 905 of the heart pump assembly 900 is connected to a motor (not shown). The motor is internal to and integrated with the motor housing 905. In other implementations the motor is external to the body and connected to the pump via a drive shaft (not shown) within a catheter 975 and in such an example the heart pump assembly 900 may not include the motor housing 905. The cannula body 909 is connected to a distal end of the motor housing 905 at the outflow section 924.

The heart pump assembly 900 can be inserted in various ways, such as by percutaneous insertion into the heart 903. For example, the intravascular heart pump system can be inserted through a femoral artery (not shown), through the aorta 976, across the aortic valve 978, and into the left ventricle 982. In certain implementations, the heart pump assembly 900 is surgically inserted into the heart 903. In some implementations, the heart pump assembly 900, or a similar system adapted for the right heart, is inserted into the right heart. For example, a right heart pump similar to the heart pump assembly 900 can be inserted through the pulmonary vein, bypassing the right atrium and right ventricle, and extending into the pulmonary artery. In certain implementations, the heart pump assembly 900 may be positioned for operation in the vascular system outside of the heart 903 (e.g., in the aorta 976). By residing minimally invasively within the vascular system, the heart pump assembly 900 is sufficiently sensitive to allow characterization of native cardiac function.

In some implementations, the heart pump assembly 900 may be sized to fit the heart of a patient. In some implementations, the cannula body 909 has a length of about 17 cm. In some implementations, the cannula body has a length of 11 cm, 12 cm, 15 cm, 17 cm, 19 cm, 20 cm, 22 cm or any other suitable length. In some implementations, the cannula body 909 has an outer diameter of less than or equal to about 22 Fr. In some implementations, the cannula body 909 has an outer diameter of 17 Fr, 19 Fr, 22 Fr, 24 Fr, or any other suitable diameter.

The flexible projection 912 is coupled to a distal end of the cannula 910, and is distal of the inflow section 916 of the heart pump assembly 900. The flexible projection 912 spaces the cannula body 906 from the walls of the heart 903 and prevents the at least one inflow aperture 914 in the inflow section 916 from suctioning to the walls of the heart 903. The flexible projection 912 may be a pigtail extension. As will be appreciated, such a device can include any of the configurations of apertures described above. The device may or may not include an atraumatic tip or flexible distal projection 912.

Figure 10:
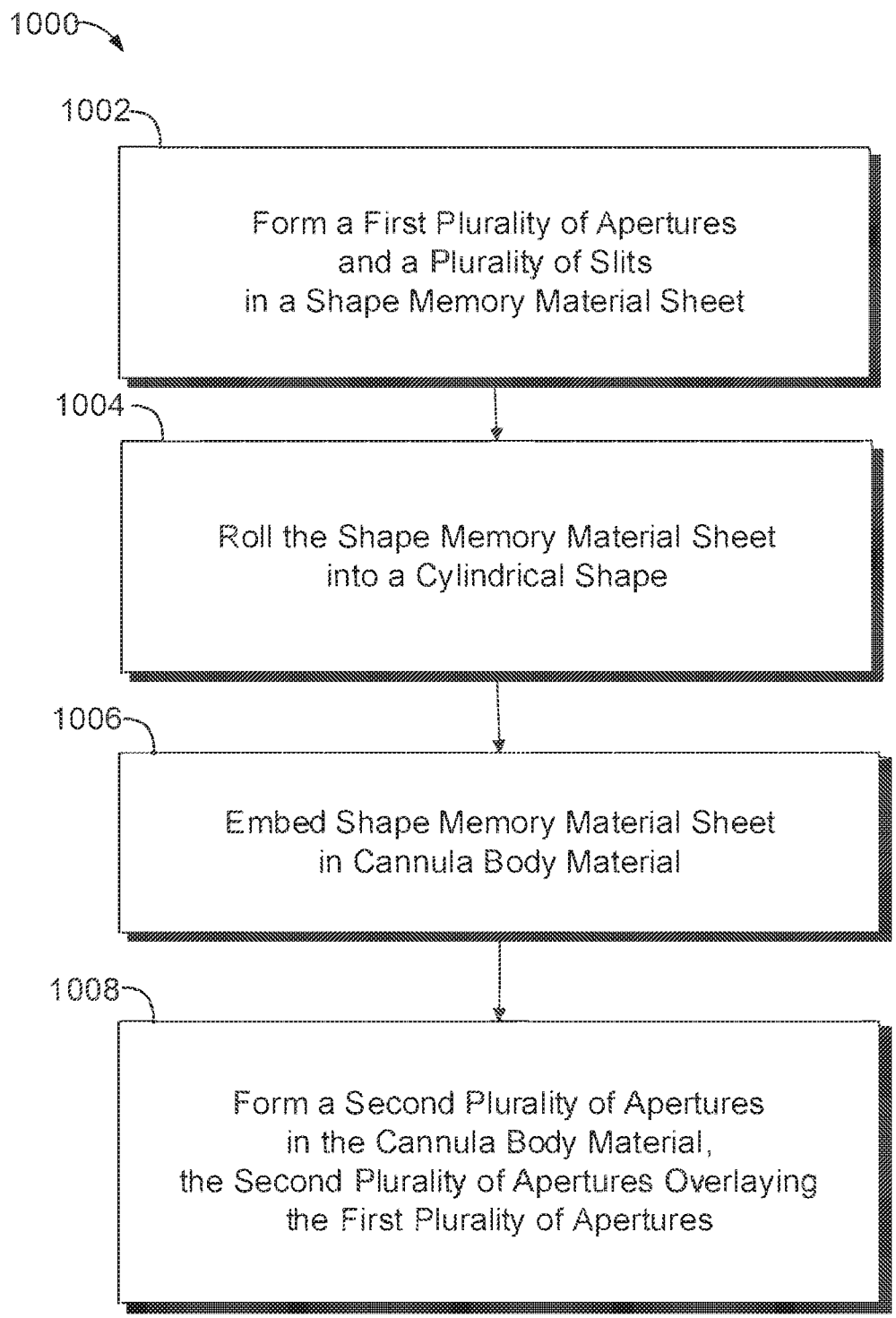
FIG. 10 shows a flow chart for a method of producing a blood inflow section of a heart pump assembly.

FIG. 10 shows a flow chart for a method of producing a blood inflow section (e.g., inflow section 116 of FIG. 1B, 216 of FIG. 2, 916 of FIG. 9, or any other suitable inflow section) of a heart pump assembly. The method 1000 may be implemented to form an inflow section from a shape memory material sheet having a plurality of apertures formed therein. In step 1002 a plurality of inflow apertures and a plurality of slits are formed in a shape memory material sheet. The apertures may be all the same size and shape, or may be a variety of sizes and/or shapes. The apertures may be formed in any number or pattern and may be any suitable shape, such as a circle, an oblong shape, a tear drop shape. The apertures may be aligned along an axis or may be offset from one another. The shape memory material sheet may be nitinol. In some implementations, the shape memory material sheet is 0.07 mm in thickness. In some implementations, the shape memory material sheet has a thickness less than or equal to 0.03 mm, 0.05 mm, 0.07 mm, 0.09 mm, 0.1 mm, 0.2 mm, 0.25 mm or any other suitable thickness.

As with the plurality of apertures, the plurality of slits may all be the same size and shape or they may be a variety of sizes and/or shapes of a configuration designed to enable the pump to flex. The plurality of slits may be oblong in a uniform direction on the shape memory material sheet. The slits may be arranged between the plurality of apertures, and/or may be proximal or distal to the apertures. The holes provide increased flexibility of the shape memory material in the region of the holes.

At step 1004, the shape memory material sheet is rolled or formed into a cylindrical shape. The rolled shape memory material sheet forms the inflow section or inflow cage/basket of the cannula body. The shape memory material sheet is curved to form a cylinder such that a first side edge of the memory material sheet meets or approaches a second opposite side edge. The distal end of the sheet and proximal end of the sheet form the ends of the cylinder to which the shape memory coil may be attached.

At step 1006, the shape memory material sheet is embedded in a cannula body material. The cannula body material may be a plastic material, such as polyurethane, or any other suitable plastic. Embedding the shape memory material sheet in the cannula body material may include embedding the shape memory material sheet between a first layer of the cannula body material and a second layer of the cannula body material. In some implementations, the embedded shape memory material sheet and cannula body material has a thickness of 0.05 mm, 0.07 mm, 0.09 mm, 0.1 mm, 0.2 mm, 0.25 mm, 0.3 mm, 0.5 mm or any suitable thickness.

At step 1008, a second plurality of apertures is formed in the cannula body material such that each of the first plurality of apertures and each of the second plurality of apertures overlay. In some implementations, an outer perimeter of each of the second plurality of apertures is within an outer perimeter of one of the first plurality of apertures. In some implementations, the outer perimeter of each of the second plurality of apertures extends beyond the outer perimeter of each of the first plurality of apertures by 0.5 mm, 1 mm, 2 mm, 3 mm, 4 mm, 5 mm, or any suitable distance. In some implementations, the first plurality of apertures and the second plurality of apertures are the same or a similar shape. In some implementations, the first plurality of apertures and the second plurality of apertures have substantially different shapes. In some implementations, the first plurality of apertures and the second plurality of apertures are formed simultaneously.

In some implementations, an edge of each of the second plurality of apertures is rounded, beveled, or chamfered. In some implementations, the entirety of the edge of each aperture in the shape memory material sheet forming is embedded in the polymer cannula body. In some implementations, only a portion of the edge of each aperture in the shape memory material sheet is embedded in the cannula body material. For example, a proximal edge of the shape memory material sheet forming/surrounding a first aperture may be fully embedded in the polymer cannula body material forming a smooth surface that prevents damage to blood entering the cannula.

The foregoing is merely illustrative of the principles of the disclosure, and the apparatuses can be practiced by other than the described embodiments, which are presented for purposes of illustration and not of limitation. It is to be understood that the apparatuses disclosed herein, while shown for use in percutaneous heart pumps, may be applied to apparatuses in other applications requiring reinforcement of section subject to squeezing forces while maintaining a clear aperture for inflow.

Variations and modifications will occur to those of skill in the art after reviewing this disclosure. The disclosed features may be implemented, in any combination and subcombination (including multiple dependent combinations and sub-combinations), with one or more other features described herein. The various features described or illustrated above, including any components thereof, may be combined or integrated in other systems. Moreover, certain features may be omitted or not implemented.

Examples of changes, substitutions, and alterations are ascertainable by one skilled in the art and could be made without departing from the scope of the information disclosed herein. All references cited herein are incorporated by reference in their entirety and made part of this application.

I claim:

1. A method for producing a blood inflow section, comprising:
    forming a first plurality of apertures and a plurality of slits in a shape memory material sheet;
    rolling the shape memory material sheet into a cylindrical shape;
    embedding the shape memory material sheet in a polymer material to form a cannula body; and
    forming a second plurality of apertures through the cannula body, wherein each of the first plurality of apertures and the second plurality of apertures overlay;
    wherein embedding the shape memory material sheet in a polymer material comprises embedding the shape memory material sheet between a first polymer layer and a second polymer layer.

2. The method of claim 1, wherein an outer perimeter of each of the second plurality of apertures is within an outer perimeter of one of the first plurality of apertures.

3. The method of claim 2, wherein the shape memory material sheet is formed of nitinol.

4. The method of claim 1, wherein an outer perimeter of each of the second plurality of apertures extends beyond an outer perimeter of each of the first plurality of apertures by at least 0.5 mm.

5. The method of claim 1, wherein the first plurality of apertures and the second plurality of apertures are of the same shape.

6. The method of claim 1, wherein the first plurality or apertures and the second plurality of apertures have substantially different shapes.

7. The method of claim 1, wherein the first plurality of apertures and the second plurality of apertures are formed simultaneously.

8. The method of claim 1, wherein an edge of each of the second plurality of apertures is any one of: rounded, beveled, or chamfered.

9. The method of claim 1, wherein at least a portion of an edge of each of the second plurality of apertures is embedded in the cannula body material.

10. The method of claim 1, wherein the cannula body has an outer diameter of less than or equal to about 22 Fr.

11. The method of claim 1, wherein the memory material sheer is less than or equal to 0.07 mm thick.

* * * * *